(12) United States Patent
Jeffries et al.

(10) Patent No.: US 8,889,721 B2
(45) Date of Patent: Nov. 18, 2014

(54) CLOTHIANIDIN, METOFLUTHRIN, AND PIPERONYL BUTOXIDE MIXTURE FOR BED BUG CONTROL

(71) Applicant: Valent BioSciences Corporation, Libertyville, IL (US)

(72) Inventors: David Jeffries, Hebron, IL (US); Deanna Branscome, Lake Villa, IL (US)

(73) Assignee: McLaughlin Gormley King Company, Golden Valley, MN (US)

( * ) Notice: Subject to any disclaimer, the term of this patent is extended or adjusted under 35 U.S.C. 154(b) by 99 days.

(21) Appl. No.: 13/767,084

(22) Filed: Feb. 14, 2013

(65) Prior Publication Data
US 2013/0210871 A1    Aug. 15, 2013

Related U.S. Application Data

(60) Provisional application No. 61/598,475, filed on Feb. 14, 2012.

(51) Int. Cl.
| | | |
|---|---|---|
| *A01N 43/78* | (2006.01) | |
| *A01N 43/30* | (2006.01) | |
| *A01N 37/36* | (2006.01) | |
| *A01N 53/00* | (2006.01) | |
| *A01N 51/00* | (2006.01) | |

(52) U.S. Cl.
CPC ............... *A01N 43/78* (2013.01); *A01N 53/00* (2013.01); *A01N 43/30* (2013.01); *A01N 51/00* (2013.01); *A01N 37/36* (2013.01)
USPC ........................... 514/365; 514/464; 514/531

(58) Field of Classification Search
None
See application file for complete search history.

(56) References Cited

U.S. PATENT DOCUMENTS

| | | |
|---|---|---|
| 2005/0124492 A1 | 6/2005 | Asrar et al. |
| 2008/0027046 A1 | 1/2008 | Annan et al. |
| 2009/0182040 A1 | 7/2009 | Heger et al. |
| 2011/0080255 A1 | 4/2011 | Borth et al. |

OTHER PUBLICATIONS

International Search Report and Written Opinion issued by the International Bureau on Apr. 26, 2013.
Valent BioSciences, "Notice of Pesticide: VBC3 Insecticide," United States Environmental Protection Agency [online], Sep. 25, 2012 [retrieved on Apr. 4, 2013], pp. 1-11.

*Primary Examiner* — James D Anderson
(74) *Attorney, Agent, or Firm* — Wood, Phillips, Katz, Clark & Mortimer

(57) ABSTRACT

The invention relates to a mixture comprising clothianidin, metofluthrin, and piperonyl butoxide which provides superior insect knockdown and mortality rates, and is especially effective against bed bugs. This mixture of actives may be formulated with adjuvants, such as solvents, anti-caking agents, stabilizers, defoamers, slip agents, humectants, dispersants, wetting agents, thickening agents, emulsifiers, and/or preservatives which increase the activity of the mixture. Mixtures of the present invention have long lasting residual control.

8 Claims, No Drawings

CLOTHIANIDIN, METOFLUTHRIN, AND PIPERONYL BUTOXIDE MIXTURE FOR BED BUG CONTROL

FIELD OF THE INVENTION

The present invention is directed to a combination of clothianidin, metofluthrin, and piperonyl butoxide that provides superior insect knockdown and mortality rates, and is especially effective against bed bugs. This mixture of actives may be formulated with adjuvants, such as solvents, anti-caking agents, stabilizers, defoamers, slip agents, humectants, dispersants, wetting agents, thickening agents, emulsifiers, and/or preservatives which increase the long lasting activity of the actives.

BACKGROUND OF THE INVENTION

The present mixture is generally directed to a safe and significantly more effective treatment for insect control. Additionally, the present mixture provides quick knockdown of insects, a high mortality rate, and long-lasting residual control.

Synanthropic insect infestations are a persistent problem. Many insects are difficult to detect until the population is very large and poses a significant threat to human health and welfare. Bed bugs (*Cimex lectularius*) are under investigation as biological and mechanical vectors of human disease and there have been documented cases of them carrying antibiotic resistant *Staphylococcus aureus*.

Bed bugs are difficult to detect because they are small, cryptic pests and are usually nocturnal. Currently, there are a limited number of means for capturing and containing bed bugs. Often, use of insecticides is the only way to thoroughly treat an environment and provide effective, long-lasting control.

However, the insecticides currently registered are often reported to provide inadequate residual control of bed bugs. Residual control is in reference to control, mitigation and/or prevention of infestations after the date of initial treatment. True residual control provides protection against re-infestation for at least, if not exceeding, 30 days after treatment. Applicants' mixture surprisingly provided improved residual efficacy against pyrethroid resistant, pyrethroid susceptible, and wild-type, field strain bed bugs.

True residual control is difficult to achieve with currently registered insecticides due to resistance found amongst bed bug populations. Bed bug resistance to synthetic pyrethroids has been thoroughly documented in populations of bugs obtained from field sites. Therefore, efforts to enact bed bug control measures using traditional and available insecticides are often ineffective due to the inherent resistance profiles encountered by pest management professionals (PMPs) and consumers of household insecticides.

Resistance is a complex phenomenon arising from exposure to the same or similar insecticide class over a period of multiple insect generations. Resistance develops due to extinction of susceptible individuals within the population and survival with subsequent reproduction of individuals who are inherently "immune" to the effects of the insecticide. Resistance can be due to multiple factors to include target site mutations, selection of detoxification enzymes and decreased cuticular penetration. Resistance may arise in nave populations that have been previously identified as insecticide susceptible or those which have been exposed to insecticides of another or similar class or mode of action. Cross resistance can occur and in addition to physiological resistance, behavioral resistance mechanisms may also be present. The end result of current control measures is that available insecticides are often inadequate to provide the mortality rates necessary to completely eliminate or collapse then insect population. As the Environmental Protection Agency ("EPA") has determined that pyrethroid-resistant colonies pose a significant human health risk, there is a need in the art for a safe and effective insect control formulation that provides superior bed bug control.

SUMMARY OF THE INVENTION

Applicants have discovered a mixture that provides improved insect control. Applicants' mixture controls pyrethroid-resistant, pyrethroid susceptible, and wild-type, field strain bed bugs. The mixture kills bed bugs of all life stages, and importantly, provides long lasting residual control.

In one aspect, the present invention is directed to a mixture comprising clothianidin, metofluthrin, and piperonyl butoxide, that can optionally be formulated with adjuvants, such as solvents, anti-caking agents, stabilizers, defoamers, slip agents, humectants, dispersants, wetting agents, thickening agents, emulsifiers, and preservatives.

In another aspect, the present invention is directed to a formulation comprising clothianidin, metofluthrin, and piperonyl butoxide, with adjuvants such as solvents, wetting agents, emulsifiers, anticaking agents, defoamers, thickening agents, and preservatives.

In a further aspect, the present invention is directed to methods of controlling insects by applying the mixture formulated with adjuvants to an environment. For example, the formulated mixture can be sprayed or brushed, onto a surface that is infested, or could be infested, with insects.

Finally, the present invention is directed to a mixture and methods of using the mixture to safely provide improved residual bed bug control.

DETAILED DESCRIPTION OF THE INVENTION

The present invention is directed to a mixture of clothianidin, metofluthrin, and piperonyl butoxide ("PBO") that works with adjuvants to quickly knockdown and kill insects during all life stages.

Clothianidin ((E)-1-(2-chloro-1,3-thiazol-5-ylmethyl)-3-methyl nitroguanidine) (available from Sumitomo Chemical Co., Tokyo, JP) is a member of the nitroguanidine subgroup of nicotinoid insecticides. Clothianidin attacks the central nervous system of insects and the EPA considers clothianidin less harmful to humans, mammals and aquatic animals than organophophate and carbamate insecticide alternatives. Clothianidin has traditionally been used as a seed treatment to protect seeds from damage caused by chewing and sucking insects.

Metofluthrin (available from Sumitomo Chemical Co., Tokyo, JP) is fast-acting pyrethroid that is also vapor-active, Metofluthrin can penetrate an insect's exoskeleton via uptake through the spiracles and possibly by transport through dermal pores, along wax canals or through other mechanisms not yet known. Metafluthrin causes paralysis by attacking the insect's central nervous system. Metofluthrin has historically been used for mosquito knockdown and repellency.

PBO (available from Endura SPA, Bologna, IT) prevents insects from recovering from pyrethroid exposure by inhibition of metabolizing enzymes, Thus, PBO increases the effectiveness and toxicity of metofluthrin. However, PBO demonstrates little or no insecticidal effects if applied alone.

Mixtures of the present invention can generally contain a ratio of clothianidin:metofluthrin:PBO that is from 1:0.001:0.25 to 20:0.4:40. Preferably, this ratio is from 10:0.25:2.5 to 10:0.4:40. Most preferably, this ratio is 4:0.1:10.

Formulations of the present invention generally comprise clothianidin, metofluthrin, PBO, and may contain adjuvants, such as solvents, anti-caking agents, stabilizers, defoamers, slip agents, humectants, dispersants, wetting agents, thickening agents, emulsifiers, and preservatives which increase the long lasting activity of the actives. Other components that enhance the biological activity of these ingredients may optionally be included.

Formulations of the present invention preferably contain from about 0.001 to 12% weight clothianidin. More preferred is a formulation that contains from about 2 to 12% weight clothianidin. Presently, clothianidin is most preferred at about 4.0% weight of the formulation.

Formulations of the present invention preferably contain from about 0.0001 to 10% weight metofluthrin. More preferred is a formulation that contains from about 0.01 to 0.12% weight metoflutlarin. Presently, metofluthrin is most preferred at about 0.10% weight of the formulation.

Formulations of the present invention preferably contain from about 0.001 to 25% weight PBO. More preferred is a formulation that contains from about 1 to 20% weight PBO. Presently, PBO is most preferred at about 10.0% by weight.

Formulations of the present invention can contain a solvent. Examples of solvents include water, glycerol, and propylene glycol. The preferred total amount of the solvent is from about 75 to 90% weight of the formulation.

Formulations of the present invention can contain an anti-caking agent. An example of an anti-caking agent is hydrophilic fumed silica. The preferred total amount of the anti-caking agent is about 0.5 to 2.0% weight of the formulation.

Formulations of the present invention can contain a dispersion stabilizer. Examples of dispersion stabilizers include polyvinyl alcohol and polyvinyl pyrrolidone. The preferred total amount of the dispersion stabilizer is about 0.05 to 0.15% weight of the formulation.

Formulations of the present invention can contain a defoamer. Examples of defoamers include silicone emulsions. The preferred amount of the defoamer is about 0.005 to 0.15% weight of the formulation.

Formulations of the present invention can contain a slip agent. One example of a slip agent is carnauba wax emulsion. The preferred total amount of the slip agent is about 0.10 to 0.30% weight of the formulation.

Formulations of the present invention can contain a humectant. One example of a humectant is sorbitol. The preferred total amount of the humectant is about 0.25 to 0.5% weight of the formulation.

Formulations of the present invention can contain a dispersant. Acrylic graft copolymers are a type of dispersant. The preferred total amount of the dispersant is about 0.1 to 0.25 weight of the formulation.

Formulations of the present invention can contain a wetting agent. Examples of wetting agents include tristyrlphenol phosphates and polyalkoxylated buty ether. The preferred total amount of the wetting agent is about 0.050 to 3.0% weight of the formulation.

Formulations of the present invention can contain a thickening agent. Xanthan gum, bentonite, and colloidal magnesium aluminum silicate are examples of thickening agents. The preferred total amount of the thickening agent is about 0.15 to 0.25% weight of the formulation.

Formulations of the present invention can contain an emulsifier. Examples of emulsifiers include tristyrylphenol-polyglycolether and benzenesulfonic acid salts. The preferred amount of the total emulsifier is about 0.25 to 3.5% weight of the formulation.

Formulations of the present invention can contain a preservative. Examples of preservatives include isothiazolin-3-one preservative solutions. The preferred amount of the preservative is about 0.06 to 0.15% weight of the formulation.

Formulations of the present invention may be further diluted for use.

Applicants surprisingly discovered that a mixture of clothianidin, metofluthrin, and PBO allowed for a significantly improved insecticide that could be used safely in residential and commercials buildings. Applicants surprisingly discovered that this mixture when formulated was especially effective in killing be bugs during all life stages: eggs, nymphs and adults. Further, Applicants surprisingly found that the mixture of clothianidin, metofluthrin, and PBO worked against those insects that had been identified as having a pyrethroid resistance ratio of several hundred to several thousand times that of susceptible insects. The efficacy was most pronounced when quantitatively examined during residual contact activity. Additionally, insects succumbed to the effects of the formulated mixture after only a brief duration of exposure (5 min). Typically, exposures to insecticides will occur for longer than 5 minutes. Applicants also surprisingly discovered that the insects are not repelled by the formulated mixture and will remain in contact with treated surfaces, thus maximizing potential uptake of the insecticide by the insects.

Applicants surprisingly discovered that the mixture when formulated has many additional benefits besides being effective for insect control. For example, the formulation does not stain upholstery or fabrics and does not leave a visible residue. Because insects, and especially bed bugs, typically can be found on upholstered materials and on mattresses, it is important that the insect control formulation does not permanently damage the owner's belongings. Also, the formulation has a very low detectable odor following application. This reduces the inconvenience of waiting a long time before re-entering a space following treatment. These characteristics are desirable because without them, the product would not be suitable for residential or commercial use.

Applicants also surprisingly found that the mixture provided residual control for at least four weeks. This characteristic of the mixture reduces the frequency of treatments which provides increased cost savings and minimizes the inconveniences of frequent treatments.

Further, Applicants found that the mixture allowed for quick knockdown of the insects. Knockdown is the stage that proceeds death and is characterized by an insect's inability to right itself when on its dorsum or make coordinated forward movements. Because clothianidin and metofluthrin work on the insects' central nervous system, they immobilize and/or severely inhibit normal activity of the insects within minutes. Previously, insects treated with formulations of the prior art would continue to be mobile for up to a day or longer following contact with the formulation. Delayed knockdown allows for the insects to continue to bite, breed, and move to new locations prior to onset of noticeable effects. It also gives the appearance of ineffective insecticidal qualities and increases the time until human re-inhabitation and clean up can occur.

Another embodiment of the present invention is methods of using the formulations of the present invention for insect control. A preferred method of applying the formulations of the present invention is by spraying, brushing, or other application which distributes the liquid product to the environment in need of treatment. Presently, the most preferred methods of application are by spraying or brushing an effective amount of the formulation onto a surface.

The mixture of the present invention can be applied to any environment in need of insect control. The environment in need of insect control may include any area that is desired to be free of insect infestation. For example, the formulation can be applied to an environment such as residential or commercial buildings, including single family dwellings, hotels, daycares, libraries, multi-family residences, jails, hostels, wash rooms, hallways, including hotels, and hospitals, or transportation vehicles.

The disclosed, embodiments are simply exemplary embodiments of the inventive concepts disclosed herein and should not be considered as limiting, unless the claims expressly state otherwise.

As used herein, all numerical values relating to amounts, weight percentages and the like are defined as "about" or "approximately" each particular value, namely, plus or minus 10%. For example, the phrase "at least 5% by weight" is to be understood as "at least 4.5% to 5.5% by weight." Therefore, amounts within 10% of the claimed values are encompassed by the scope of the claims.

The term "effective amount" means the amount of the formulation that will kill the insect. The "effective amount" will vary depending on the formulation concentration, the type of insect(s) being treated, the severity of the insect infestation, the result desired, and the life stage of the insects during treatment, among other factors. Thus, it is not always possible to specify an exact "effective amount." However, an appropriate "effective amount" in any individual case may be determined by one of ordinary skill in the art.

The present invention includes concentrated formulations that can be easily prepared and then sold and distributed to an end user. Utilizing high concentrations for shipping and handling allows the use of smaller volumes of solvent, thus simplifying shipping and handling procedures and decreasing costs. The end user can apply formulations of the present invention to environments by diluting the formulation to a desired concentration prior to application of the formulation to an environment. Alternatively, the diluted solution could be prepared and provided to the end for application to an environment.

Examples of representative packaging formats include ready-to-use packages such as concentrates: non-pressurized containers such as liquids and gels; aerosols and various solid forms such as dusts, powders and granules. Examples of controlled-release formulations include paints, glue boards, baits, bait stations, blocks, pellets, time-release membranes, traps and strips.

The following examples are intended to illustrate the present invention and to teach one of ordinary skill in the art how to use the formulations of the invention. They are not intended to be limiting in any way.

EXAMPLES

Example 1

A Formulation of Clothianidin, Metofluthrin, and Piperonyl Butoxide was Prepared First, a clothianidin premix was prepared by agitating clothianidin with water, polyvinyl alcohol, glycerol, sorbitol solution, a surfactant, tristyrylphenol phosphate, tetramethyl decyne diol, xanthan gum, carnauba wax emulsion, an isothiazolin-3-one preservative, and a defoamer. The clothianidin premix then passed through a bead mill to produce a finished base with a median particle size of <5 microns. A metofluthrin premix was prepared by charging propylene glycol in a stainless steel vessel and then adding metofluthrin, dodecyl benzene sulphonate salt, and tristyrylphenol-polyglycolether. Once the metofluthrin premix was homogeneous, water was added followed by a preservative.

Following preparation of the clothianidin premix and the metofluthrin premix, the final formulation was mixed. First, the clothianidin premix was charged in a stainless steel vessel. Then, the following ingredients were added in the following order PBO; xanthan gum premixed with water; hydrophilic fumed silica with agitation; the metofluthrin premix; and finally an isothiazoline-3-one preservative. The formulation was then mixed until homogeneous and stored until use. The formulation can be diluted to all appropriate amount prior to use.

Example 2

A bioassay was performed to determine the repellency of the Formulation of Example 1 to bed bugs. Tent-like harborages were made by folding 4 cm×2.5 cm pieces of cardstock lengthwise. The harborages were treated with the Formulation of Example 1, deionized water, or no treatment. Treated harborages were allowed to dry for 72 hours and then the harborages were placed in Petri dishes (150×25 mm), and then the Petri dishes were placed in clear Pyrex dishes.

Twenty-two adult bed bugs, ½ males and ½ females, were placed in each treatment dish for 5 minutes to determine which harborage was the most attractive to the bed bugs. The following bioassays were completed: the Formulation of Example 1 and no treatment; and deionized water and no treatment. Using Chi-square analysis with SAS software v. 9.2, the following results were determined.

The bedbugs were marginally attracted to the Formulation of Example 1 compared to the untreated and deionized water controls ($p=0.0881$). Therefore, it has been found that the Formulation of Example 1 is non-repellent. This result was unexpected because the Formulation of Example 1 contains metofluthrin, a known insect repellent. This surprising result means that bed bugs will not be repelled and relocate to an untreated environment when exposed to the Formulation of Example 1. Therefore, the Formulation of Example 1 is an improvement over prior art insecticides that repel insects.

Example 3

Another bioassay was performed to determine the knockdown and mortality rates of bed bugs exposed to the residual of the Formulation of Example 1. Two bed bug strains were used Jersey City-strain which is known to have 1000-fold resistance to deltamethrin, and Winston Salem-strain which is known to have a 500-fold resistance level to deltamethrin (a commonly used pyrethroid). In this bioassay, the Formulation of Example 1 was compared to a water control. All tests were done in 4 replicates (40 insects total per treatment).

Unpainted wood was cut into 6 inch square panels and a DeVries spray booth was used to deliver 1 ml of test substance in an even spray that provided approximately 1 gal/1000 sq. ft. delivery rate. A cone-jet nozzle was used approximately 12 inches directly above the wood panels. The panels were allowed to dry and then aged indoors for 1 day to 34 days in a climate controlled environment with temperatures ranging from approximately 65 to 72 degrees Fahrenheit.

Insects were fed a blood meal the day prior to testing. The inner walls of Petri dishes were treated with Fluon to prevent the insects from attaching to the sides of the dishes during treatment.

On the day of testing, 10 mixed-sex insects were placed in each Petri dish. The bed bugs were separated with tweezers and observed to be healthy and active before treatments. The Petri dishes were inverted onto the treated surface and gentle tapping was sometimes used to dislodge the insects from the dishes. After 5 minutes, the insects were returned to containers for knockdown and mortality observations. Observations were taken until untreated control mortality reached 10 percent.

For Jersey City-strain bed bugs at the 1 Day residual testing, the Formulation of Example 1 provided $KT_{50}$ of less than 10 minutes; $KT_{90}$ of less than 20 minutes; and 100 percent mortality by 24 hours. For the 34 Day residual testing, the Formulation of Example 1 provided $KT_{50}$ of 15.5 minutes; $KT_{90}$ of 1.4 hours; and 100 percent mortality by 3 days post treatment. Therefore, it was determined that the Formulation of Example 1 provided residual kill efficacy against pyrethroid-resistant Jersey City-strain bed bugs.

For the Winston Salem-strain bed bugs at the 1 Day residual testing, the Formulation of Example 1 provided $KT_{50}$ of less 35 min; $KT_{90}$ of less than 2 days; and 100 percent mortality by three days post treatment. For the 30 Day residual testing, the Formulation of Example 1 provided $KT_{50}$ of 1.6 hours; $KT_{90}$ of 1.4 days; and 100 percent mortality by 4 days post treatment. Therefore, it was determined that the Formulation of Example 1 provided residual kill efficacy against pyrethroid-resistant Winston Salem-strain bed bugs.

Example 4

This bioassay was performed to determine the knockdown and mortality rates of bed bugs directly exposed to the Formulation of Example 1. Two bed bugs strains were used; Jersey City-strain, and Winston Salem-strain. In this bioassay, the Formulation of Example 1 was compared to a water control. All tests were done in 4 replicates (40 insects per treatment).

Ten mixed-sex bed bugs were placed into 8 ounce Fluon coated cups. One ml of the liquid formulation was applied using a compressed-air sprayer by holding the nozzle approximately 12 inches away from the bed bugs. Treated bugs were observed for knockdown at 15, 30, 45, and 60 seconds and 2, 3, 4, and 5 minutes after application. After 5 minutes, the bed bugs were transferred to clean containers.

For Jersey City-strain bed bugs, the Formulation of Example 1 provided $KT_{50}$ of 13 seconds; $K_{90}$ of 1.4 minutes; and 100 percent mortality by 24 hours post treatment. Therefore, it has been determined that the Formulation of Example 1 provided direct contact kill efficacy against pyrethroid-resistant Jersey City-strain bed bugs.

For the Winston Salem-strain bed bugs, the Formulation of Example 1 provided $KT_{50}$ of 57 seconds; $KT_{90}$ of 2.9 minutes; and 100 percent mortality by 24 hours post treatment. Therefore, it has been determined that the Formulation of Example 1 provided direct contact kill efficacy against pyrethroid-resistant Winston Salem-strain bed bugs.

Example 5

The Formulation of Example 1 was tested to determine its kill efficacy following direct application to bed bug eggs. Two bed bug strains were used; Harlan-strain and Winston Salem-strain.

Ten bed bug eggs were placed into 8 ounce Fluon coated cups. One ml of the liquid formulation was applied using a compressed-air sprayer by holding the nozzle approximately 12 inches away from the bed bug eggs. After 5 minutes, the eggs were transferred to clean containers. The control eggs were treated in the same way except the were sprayed with water. Treated eggs were kept in an incubator at 23-38 degrees Celsius and 25-70 percent relative humidity. The eggs were checked daily until the hatch rate in untreated controls reached 90 percent. Each test was done in 4 replicates (40 total eggs per treatment).

For Harlan-strain and Winston Salem-strain bed bug eggs exposed to the Formulation of Example 1, there were no hatchings and a 100% kill rate. The Harlan-strain water control reached a 92.5% hatch rate at 6 days post treatment and the Winston Salem-strain water control reached a 90% hatch rate at 9 days. Therefore, it has been determined that the Formulation of Example 1 is an effective bed bug egg control treatment.

Example 6

This bioassay was also performed to determine the mortality rates of bed bugs directly exposed to the Formulation of Example 1. Two bed bug stains were used; a "Susceptible" strain; and a "Frank 1" wild type strain. "Frank 1" is known to be highly pyrethroid-resistant. There were four replicates for each substance with 10 bed bugs being tested in each replication (total of 40 bed bugs exposed to each substance). In this bioassay, the Formulation of Example 1 was compared to a water control.

The insects were immobilized and transferred into 1.75 inch diameter CPVC cartridges that were ½ inch thick. The cartridges were covered with BioQuip 7250NSW mesh that was secured in place. Once all of the insects were confirmed alive and mobile, the treatment began. For the water control and Formulation of Example 1 treatments, the spray applicator was placed approximately 12 inches from the cartridges and sprayed at a rate of approximately 1 gal/1000 square feet.

One hour following treatment, the insects were transferred to clean Petri Dishes each containing one 1 inch×1 inch cardboard harborage. Two drops of water were placed on the cardboard harborages to provide humidity. The insects were observed at 30 minutes, 1, 2, 4, and 24 hours, and each day post treatment for up to six days. The observed mortality rates are summarized below in Table 1.

TABLE 1

Average % Mortality of Bed Bugs When Exposed to Direct Spray

| Strain | Treatment | 30 min | 1 hr | 2 hr | 4 hr | 24 hr | 2 DAT | 3 DAT | 4 DAT | 5 DAT | 6 DAT |
|---|---|---|---|---|---|---|---|---|---|---|---|
| Susceptible | Water control | 0 | 0 | 0 | 3 | 3 | 5 | 8 | 10 | 10 | NA |
| Susceptible | Form. of Ex. 1 | 83 | 100 | 83 | 80 | 55 | 90 | 98 | 100 | 100 | NA |
| Frank 1 | Water control | 0 | 0 | 0 | 0 | 0 | 0 | 0 | 0 | 0 | 0 |
| Frank 1 | Form. of Ex. 1 | 78 | 88 | 80 | 83 | 73 | 78 | 98 | 98 | 98 | 100 |

Six days after treatment, the Formulation of Example 1 had 100% mortality on both strains of bed bugs. Therefore, it has been shown that the Formulation of Example 1 is effective against "Susceptible" strain and "Frank 1" wild type strain bed bugs.

Example 7

A bioassay was performed to determine the knockdown and mortality rates of bed bugs exposed to the residual of mixtures of clothianidin, metofluthrin, and PBO. Two bed bug (*Cimex lectularius*) strains were used; Harlan-strain which is susceptible to pyrethroids, and Winston Salem-strain which is known to have a 500-fold resistance level to deltamethrin. In this bioassay, a mixture of clothianidin, metofluthrin, and PBO with fumed silica was compared to combinations of clothianidin and metofluthrin, clothianidin and PBO, and clothianidin.

Unpainted wood was cut into 6 inch square panels and a DeVries spray booth was used to deliver 1 ml of test substance in an even spray that provided approximately 1 gal/1000 sq. ft. delivery rate. A cone jet nozzle was used approximately 12 inches directly above the wood panels. The panels were allowed to dry and then aged indoors in a climate controlled environment with temperatures ranging from approximately 65 to 72 degrees Fahrenheit. All tests were done in 4 replicates (40 total insects per treatment).

Insects were fed a blood meal the day prior to testing. The inner walls of Petri dishes were treated with Fluon to prevent the insects from attaching to the sides of the dishes during treatment.

On the day of testing, 10 insects were placed in each Petri dish. The bed bugs were separated with tweezers and observed to be healthy and active before treatments. The Petri dishes were inverted onto the treated surface and gentle tapping was sometimes used to dislodge the insects from the dishes. After 5 minutes, the insects were returned to containers for mortality/morbidity and knockdown observations.

Mortality and Morbidity Results

Insects were considered moribund when they were knocked down and unable to right themselves when probed. Insects were considered dead when they had no body movement. Untreated controls were handled in the same manner except that they were exposed to water treated wood panels.

Insects were exposed to the wood panels on day 1 and day 30. Mortality and morbidity observations were taken until the untreated control mortality reached is than 10 percent (day 7 following exposure). Table 2 below provides the observed mortality and morbidity rates.

TABLE 2

Residual Efficacy at Day 1 on Winston-Salem-strain

| Treatment | % Mortality | | | % Morbidity | | | % Mortality + Morbidity | | |
|---|---|---|---|---|---|---|---|---|---|
| | 1 day | 2 day | 3 day | 1 day | 2 day | 3 day | 1 day | 2 day | 3 day |
| Water control | 0 | 0 | 0 | 0 | 0 | 0 | 0 | 0 | 0 |
| 0.4% Cloth. + 0.01% meto. + 1.0% PBO | 83 | 93 | 100 | 13 | 5 | 0 | 96 | 98 | 100 |
| 0.4% Cloth. + 0.01% meto. | 75 | 85 | 100 | 15 | 13 | 0 | 90 | 98 | 100 |
| 0.4% Cloth. + 1.0% PBO | 85 | 85 | 100 | 10 | 15 | 0 | 95 | 100 | 100 |
| 0.4% Cloth. | 60 | 60 | 87.5 | 18 | 18 | 12.5 | 78 | 78 | 100 |

During the day 1 evaluation, all of the treatments on Harlan-strain bed bugs provided 100% mortality at 1-day post treatment. As seen above in Table 1, the mixture of clothianidin, metofluthrin, and PBO provided improved mortality and morbidity rates when applied to Winston Salem-strain bed bugs.

Approximately 30 days later, bed bugs were again, exposed to the wood panels; the mortality and morbidity rates are below in Table 3.

TABLE 3

Residual Efficacy at Day 30

% Mortality/% Morbidity (Days after Treatment - DAT)

| Strain | Treatment | 1 | 2 | 3 | 4 | 5 | 6 | 7 |
|---|---|---|---|---|---|---|---|---|
| Harlan | Water control | 0/0 | 0/0 | 0/0 C | 0/0 | 0/0 | 0/0 | 5/3 |
| Harlan | 0.4% Cloth. + 0.01% meto. + 1.0% PBO | 20/80 | 55/45 | 100/0 A | NA | NA | NA | NA |
| Harlan | 0.4% Cloth. + 0.01% meto. | 20/80 | 48/53 | 100/0 A | NA | NA | NA | NA |
| Harlan | 0.4% Cloth. + 1.0% PBO | 15/73 | 48/48 | 93/87 A | 100/0 | NA | NA | NA |
| Harlan | 0.4% Cloth. | 23/75 | 68/33 | 100/0 A | NA | NA | NA | NA |
| Winston-Salem | Water control | 0/0 | 0/0 | 0/0 | 0/0 | 0/0 | 5/3 | 8/3 C |
| Winston-Salem | 0.4% Cloth. + 0.01% meto. + 1.0% PBO | 13/75 | 40/50 | 63/28 | 73/18 | 80/13 | 90/8 | 93/8 A |
| Winston-Salem | 0.4% Cloth. + 0.01% meto. | 8/55 | 18/45 | 35/33 | 35/33 | 45/25 | 55/15 | 63/13 AB |
| Winston-Salem | 0.4% Cloth. + 1.0% PBO | 5/38 | 15/33 | 40/15 | 53/8 | 60/10 | 60/10 | 63/8 AB |
| Winston-Salem | 0.4% Cloth. | 10/33 | 20/28 | 43/18 | 53/10 | 63/8 | 70/3 | 70/5 AB |

* The different letters in the same column are significantly different (P < 0.05) for the same species when mortality and morbidity rates are added.

When applied to the Harlan-strain bed bugs, all of the treatments provided 100% mortality within 4 days. The mixture of clothianidin, metofluthrin, and PBO provided mortality or morbidity in 100% of bed bugs on Day 1, and 100% mortality by Day 3.

When applied to the Winston Salem-strain bed bugs, the mixture of clothianidin, metofluthrin, and PBO was the only treatment which provided a surprising 100% mortality and morbidity rate by 7 DAT. Applicants surprisingly discovered that the mixture of clothianidin, metofluthrin, and PBO provides high morbidity and mortality rates on pyrothroid-resistant and wild-type bed bug strains.

Knockdown Results

The bed bugs were observed and recordings were taken at 10, 20, 30, 60 and 240 minutes following exposure to the wood panels. Table 4 provides the percentage of bed bugs from all 4 replicates (40 total insects per treatment) that were knocked down 10 and 240 minutes after exposure to the wood panels.

TABLE 4

Knockdown at Day 1 and Day 30

| Strain | Treatment | Day 1 @ 10 minutes | Day 1 @ 240 minutes | Day 30 @ 10 minutes | Day 30 @ 240 min |
|---|---|---|---|---|---|
| Harlan | Water control | 0 | 0 | 0 | 0 |
| Harlan | 0.4% Cloth. + 0.01% meto. + 1.0% PBO | 75 | 100 | 63 | 100 |
| Harlan | 0.4% Cloth. + 0.01% meto. | 68 | 100 | 30 | 93 |
| Harlan | 0.4% Cloth. + 1.0% PBO | 35 | 98 | 20 | 88 |
| Harlan | 0.4% Cloth. | 48 | 95 | 20 | 95 |
| Winston-Salem | Water control | 0 | 0 | 0 | 0 |
| Winston-Salem | 0.4% Cloth. + 0.01% meto. + 1.0% PBO | 23 | 80 | 0 | 50 |
| Winston-Salem | 0.4% Cloth. + 0.01% meto. | 13 | 65 | 0 | 28 |
| Winston-Salem | 0.4% Cloth. + 1.0% PBO | 0 | 65 | 0 | 25 |
| Winston-Salem | 0.4% Cloth. | 0 | 50 | 3 | 28 |

The mixture of clothianidin, metafluthrin, and PBO provided quick knockdown of both strains of bed bugs. One day after the wood panels were treated, 75% of Harlan-strain and 23% of Winston-Salem-strain bedbugs were knocked down within 10 minutes. Within four hours, 100% of Harlan-strain and 80% of Winston-Salem strain bed bugs were knocked down.

On the panels that were aged for 30 days, the mixture of clothianidin, metofluthrin, and PBO continued to have high knockdown rates at 240 minutes. This shows that the mixture of clothianidin, metofluthrin, and PBO is effective as a residual bed bug control.

The invention claimed is:

1. A pesticidal mixture comprising an effective amount of clothianidin, metofluthrin, and piperonyl butoxide.

2. The mixture of claim 1 wherein the ratio of clothianidin:metofluthrin:piperonyl butoxide is from 1.0:0.001:0.25 to 20:0.4:40.

3. The mixture of claim 1 wherein the ratio of clothianidin:metofluthrin:piperonyl butoxide is 4:0.1:10.

4. A method of insect control comprising administering to an environment in need of insect control an effective amount of the mixture of claim 1.

5. The method of claim 4 wherein the environment is a residential or commercial building or structure.

6. The method of claim 4 wherein the mixture is applied by spraying or brushing a formulation containing said mixture onto a surface.

7. The method of claim 4 wherein the insects controlled are bed bugs.

8. The method of claim 4 wherein the mixture provides residual insect control.

* * * * *